United States Patent
Deco et al.

(10) Patent No.: US 7,398,120 B2
(45) Date of Patent: Jul. 8, 2008

(54) METHOD AND ARRANGEMENT AND COMPUTER PROGRAMME WITH PROGRAMME CODE MEANS AND COMPUTER PROGRAMME PRODUCTS FOR THE ANALYSIS OF NEURONAL ACTIVITIES IN NEURONAL AREAS

(75) Inventors: Gustavo Deco, Vilassar de Mar (ES); Norbert Galm, Zorneding (DE)

(73) Assignee: Siemens Aktiengesellschaft, Munich (DE)

( * ) Notice: Subject to any disclaimer, the term of this patent is extended or adjusted under 35 U.S.C. 154(b) by 309 days.

(21) Appl. No.: 10/524,225

(22) PCT Filed: Aug. 7, 2003

(86) PCT No.: PCT/DE03/02658

§ 371 (c)(1),
(2), (4) Date: Feb. 9, 2005

(87) PCT Pub. No.: WO2004/021245

PCT Pub. Date: Mar. 11, 2004

(65) Prior Publication Data

US 2005/0261874 A1    Nov. 24, 2005

(30) Foreign Application Priority Data

Aug. 9, 2002    (DE) .............................. 102 36 641

(51) Int. Cl.
*A61B 5/04*    (2006.01)
*G06F 17/18*    (2006.01)

(52) U.S. Cl. ........................ 600/544; 702/181; 702/19

(58) Field of Classification Search ................ 600/544, 600/408, 410, 554, 555; 128/924, 922, 928, 128/920, 25; 702/181, 19; 706/25
See application file for complete search history.

(56) References Cited

U.S. PATENT DOCUMENTS

| | | | |
|---|---|---|---|
| 2001/0056231 A1* | 12/2001 | Jesmanowicz et al. | 600/410 |
| 2002/0058867 A1* | 5/2002 | Breiter et al. | 600/407 |
| 2003/0191408 A1* | 10/2003 | Montgomery, Jr. | 600/544 |

OTHER PUBLICATIONS

"Encyclopedia of Statistical Sciences, vol. 2," Cotz et al. Eds., "Cornish-Fisher and Edgeworth Expansions," Chapter 4, pp. 188-192 (1982).

"Brain Mapping: The Methods," Toga et al., Ed., Chapter 9: "Rapid MRI and Functional Applications," Cohen (1996).

Website printout for "fmri.pro" from http://www.med.uni-muenchen.de/radin/html/.

(Continued)

*Primary Examiner*—Eric F. Winakur
*Assistant Examiner*—Lawrence N Laryea
(74) *Attorney, Agent, or Firm*—Schiff Hardin LLP

(57) ABSTRACT

In a method, arrangement and computer program for analysis of neuronal activities in neuronal areas, signals are recorded, with each signal describing the neuronal activity in one of the neuronal areas. A matchable coupling forms the basis of all signals, described by the use of matchable coupling parameters that describe the statistical relationship between the signals. Probabilities for an occurrence of the signals are determined, whereby a statistical distribution is the basis of the signals. The matchable coupling parameters are determined by optimization of the probabilities, hence matched and analyzed.

14 Claims, 2 Drawing Sheets

OTHER PUBLICATIONS

Website printout for "Specification of fMRI Device" from http://www.unipublic.unizh.ch/campus/uni-news/.

"Structural Equation Modeling and Its Application to Network Analysis in Functional Brain Imaging," McIntosh et al. Human Brain Mapping 2:2-22 (1994).

"Network Analysis of Cortical Visual Pathways Mapped with PET," McIntosh et al, J. of Neuroscience, Feb. 1994, 14(2) pp. 655-666.

Functional MRI Statistical Software Packages: A Comparative Analysis, Gold et al., Human Brain Mapping, vol. 6 (1998), pp. 73-84.

"Can Meaningful Effective Connectivities Be Obtained Between Auditory Cortical Regions?" Gonçalves et al., NeuroImage 14 (2001), pp. 1353-1360.

"Large-Scale Functional Connectivity in Associative Learning: Interrelations of the Rat Auditory, Visual and Limbic Systems," McIntosh et al., J. of Neurophysiology, vol. 80, No. 6, Dec. 1998, pp. 3148-3162.

How Good is Good Enough in Path Analysis of fMRI Data? Bullmore et al., NeuroImage 11 (2002) pp. 289-301.

\* cited by examiner

METHOD AND ARRANGEMENT AND COMPUTER PROGRAMME WITH PROGRAMME CODE MEANS AND COMPUTER PROGRAMME PRODUCTS FOR THE ANALYSIS OF NEURONAL ACTIVITIES IN NEURONAL AREAS

BACKGROUND OF THE INVENTION

1. Field of the Invention

The present invention relates to analysis of neuronal activities in neuronal areas, for example of nerve structures in areas of the brain of a patient.

2. Description of the Prior Art

Knowledge about a mode of operation of a neuronal area and about an interaction of neuronal areas are fundamental to functional magnetic resonance tomography (fMRI), as described in A. W. Toga and J. C. Maziotta (Ed.), "Brain Mapping: The Methods", Ch 9: M. S. Cohen: "Rapid MRI and Functional Applications", Academic Press 1996, which is a further development of magnetic resonance tomography.

Magnetic resonance tomography is an imaging method that produces sectional images of the human body without using damaging X-rays.

Instead MR takes advantage of the behavior of body tissue in a strong magnetic field. Pathological changes in body tissue, for example in the brain or spinal cord, can be detected by this modality.

Functional disorders in body tissue, particularly in the brain of a patient, however, cannot be detected by means of conventional magnetic resonance tomography.

This is performed by functional magnetic resonance tomography or fMRI technology.

Neuronal activity in areas of the brain of a patient can be measured indirectly by means of the fMRI technique. The BOLD (Blood Oxygenation Level Dependent) signal, as it is called, is measured in individual areas of the brain, this signal relating to neuronal activity in the respective areas.

Dependencies, which stem among other things from structures in the brain, i.e. from neuronal links between nerve cells or nerve structures, exist between the neuronal activities in the areas.

The outcome of the fMRI measurements shows the course of activity of individual areas over a certain period, for example during cognitive sequences as a result of specific perception processes or motor tasks.

Functional disorders, in this case in the brain, are thus inherently contained in the fMRI signals measured.

Efficient methods for the analysis and evaluation of such fMRI measurements are desirable in order to be able to furnish evidence of possibly existing functional disorders in specific areas.

Known methods, such as described in A. R. McIntosh et al., Structural Equation Modeling and Its Application to Network Analysis in Functional Brain Imaging, Human Brain Mapping, 2:2-22, 1994, are restricted to detection of functional relationships between various areas of the brain in certain predetermined tasks such as the aforementioned perception processes or motor tasks (functional connectivity). These functional relationships are also designated functional connectivity.

In contrast to functional connectivity, however, the determination of a true physical connectivity, i.e. the determination of actually existing linking structures (of areas of the brain) independently of specific predetermined tasks, is not possible with these known methods.

A further known method of analysis for detecting functional connectivity is described below.

The object of this known method of analysis described below is the above-described detection of functional relationships between various areas of the brain in specific perception processes or motor tasks.

This known method of analysis is based on a predefined model of a brain, i.e. a predefined brain architecture.

This brain architecture, predetermined from prior knowledge, defines general functional and/or spatial dependencies between specific areas of the brain in the form of a coupling matrix S, as it is called.

The coupling matrix S has a form or structure that is fixed in accordance with the predetermined brain architecture (columns/rows) and is accordingly populated in certain, but not at all (matrix) positions, with changeable coupling strengths $S_i$. These are changeable and are matched as part of the method of analysis.

The unpopulated (matrix) positions are populated with fixed, unchangeable values, namely zero.

The coupling strengths $S_i$ describe functional dependencies respectively between two areas of the brain or the BOLD signals measured there and represent the neuronal activities there.

In this known method of analysis, the (changeable) coupling strengths Si are defined such that statistical characteristic quantities that are determined by this method of analysis from the fMRI measurements, can best be explained. Expressed differently, the probability for an occurrence of the measured data, i.e. the fMRI measurement or the BOLD signals, is maximized by means of the desired coupling strengths Si.

In this method of analysis a data point $s=s_t$ represents a totality of all BOLD signals s1, . . . , sN of the individual n areas at a point in time t or averaged over a time interval t (t=[1;T]).

The fMRI measurement includes a large number of such data points for possibly differing perception processes and/or motor tasks, for which the corresponding BOLD signals were measured.

In this known method of analysis, it is not the individual data points s1, s2, . . . , St, which are evaluated directly, but statistical characteristic quantities that emerge from these.

For a statistical distribution of the data points s1, s2, . . . , sT it is assumed that it is described fully by a multivariant normal distribution, i.e. a statistical distribution of the first order, with a mean value m and a covariance Σ:

$$P(s \mid \mu, \Sigma) = \frac{1}{\sqrt{2\pi}^N \cdot |\Sigma|} \cdot e^{-\frac{1}{2}(s-\mu)' \Sigma^{-1}(s-\mu)} \qquad (1)$$

For sufficiently long series of measurements, the occurrence of the individual data points si of s1, s2, . . . , sT can be viewed as statistically independent.

The probability P=P(s1, . . . , sT|μ, Σ) for an occurrence of all measured data points s1, . . . , sT can accordingly be written as:

$$P(s_1, \ldots, s_T \mid \mu, \Sigma) = \qquad (2)$$

$$\prod_{t=1}^{T} P(s_t \mid \mu, \Sigma) = \frac{1}{\sqrt{2\pi}^{NT} \cdot |\Sigma|^T} \cdot e^{-\frac{1}{2}\sum_{t=1}^{T}(s_t-\mu)'\Sigma^{-1}(s_t-\mu)}$$

Here, the unknown variables, the mean value μ and the covariance Σ, depend exclusively on a(brain) model that describes the measured data.

The model assumes a linear statistical relationship between the individual BOLD signals:

$$s_i = \sum_{j=1}^{N} S_{ij} s_j + \varepsilon_i \text{ for } i = 1, \ldots, N \qquad (3)$$

or $$s = Ss + \varepsilon$$

where ε designates the external influence on the individual BOLD signals, like a sensory input of sensory cells on the examined areas of the brain.

The influence variables $\varepsilon_i$ and $\varepsilon_j$ on different examined areas i and j can in this case be correlated throughout.

The model parameters to be specified are consequently the coupling strengths $S_i$ of the underlying coupling matrix S, the mean value με of the external influence ε and the covariance Σε of ε.

The mean value μ and the covariance Σ depend on these:

$$\mu = \mu(S, \mu_\varepsilon)$$

$$\Sigma = \Sigma(S, \Sigma_\varepsilon) \qquad (4)$$

In this known method of analysis the model parameters are then determined such that the probability P=P(s1, ..., sT|μ,Σ) given in (2) for the occurrence of the measured data is maximized.

For this purpose, a known maximum likelihood estimation method (optimization) is applied such as described in T. W. Anderson, An Introduction to Multivariable Statistical Analysis, Chapter 3, John Wiley & Sons, Inc., New York, London, Sydney, 1994.

Using the relationships (4) in (2), an expression that is dependent on the coupling strengths $S_j$, the mean value με and the covariance Σε is obtained, which expression is maximized by the optimization.

The optimization then leads to the desired coupling strengths $S_i$ between the BOLD signals.

These in turn enable detection of functional relationships between various areas of the brain in specific perception processes or motor tasks (functional connectivity).

This known method of analysis exhibits the disadvantage that the measured fMRI signals are able to be modeled only insufficiently accurately or that the model is matchable only insufficiently accurately to the measured fMRI signals, and consequently the mode of operation or interaction of neuronal areas is only insufficiently mappable. This shortcoming could possibly lead to incorrect conclusions being made with regard to connective functionality.

A software tool for fMRI analysis, an "fmri.pro", is known from Specification for "fmri.pro" software relating to quantitative fMRI analysis, obtainable on Jul. 9, 2001, under http://www.med.uni-uenchen.de/radin/html/arbeitsgruppen/fmri/ccfmri.html. A device for implementing the fMRI technique is known from Specification of fMRI—device, obtainable on Jul. 9, 2001, under http://www.unipublic.unizh.ch/campus/uninews/2001/0147/fmri.html.

SUMMARY OF THE INVENTION

An object of the present invention is to provide an improved method for the analysis of neuronal activities. The improved method of analysis is intended to be able to better explain measured fMRI signals and thus to better describe the mode of operation and interaction of neuronal areas than is the case with the above-described known method of analysis.

This object is achieved in accordance with the invention by a method for the analysis of neuronal activities in neuronal areas using signals describing the neuronal activities, wherein signals are determined with each signal describing the neuronal activity in one of the neuronal areas.

A matchable coupling that is described by using matchable coupling variables that describe a statistical relationship between the matchably coupled signals forms the basis of all the signals, rather than just some of them.

Probabilities for an occurrence of the signals are determined, whereby a statistical distribution forms the basis of the occurrence of the signals.

All matchable coupling variables are determined by an optimization of the probabilities and hence matched.

The neuronal activities are analyzed using the matchable coupling variables.

The arrangement in accordance with the invention for the analysis of neuronal activities in neuronal areas by the use of signals describing the neuronal activities has units connected with one another which are configured such that the signals can be determined, whereby each signal describes the neuronal activity in one of the neuronal areas, a matchable coupling can form the basis of all, not just some of the signals, said matchable coupling being described by using matchable coupling variables which describe a statistical relationship between the matchably coupled signals, probabilities for an occurrence of the signals can be determined, whereby a statistical distribution forms the basis of the occurrence of the signals, all matchable coupling variables can be determined by an optimization of the probabilities and hence matched, the neuronal activities can be analyzed using matchable coupling variables.

It is essential to the invention that the matchable coupling, which is described by using the matchable coupling variables, forms the basis of all signals. By this means, absolutely all coupling variables are determined by the optimization of probabilities and hence matched.

The invention thus differs from the known method of analysis described above because in the known method matchable statistical coupling forms the basis of only some of the signals.

Only these can be determined by means of the optimization of probabilities and hence matched.

Thus, the known method of analysis presupposes a known, predetermined and stipulated neuronal structure.

In contrast to this, no predetermined and fixed coupling structures are assumed in advance by the inventive approach. These emerge only within the context of the optimization.

Through the interaction of an optimization method and a search method, i.e. the search for existing couplings and the determination of their optimum values, in the inventive approach both the coupling structure most probable on the basis of the signals and a coupling strength of the specific couplings are determined.

A particularly advantageous aspect of the inventive approach is that this approach is independent of other methods and of possibly defective prior knowledge. No prior knowledge, or just outline prior knowledge, of coupling structures is needed in the case of the invention in order to analyze the neuronal activities.

As a result of the flexibility achievable by the invention in the matching of couplings, neuronal structures can be determined with greater precision and in greater detail.

The computer program with program code according to the invention is equipped to perform all steps in accordance with the method of analysis of the invention when the program is run on a computer.

The computer program product with program code stored on a machine-readable medium is equipped to perform all steps in accordance with the method of analysis of the invention when the program is run on a computer.

The arrangement and the computer program with program code that are equipped to perform all the steps in accordance with the inventive method of program product are particularly suitable for performing the method of analysis according to the invention or one of its further developments explained below.

The further embodiments described below relate both to the methods and to the arrangement.

The invention and the further embodiments described below can be implemented both in software and in hardware, for example using a special electrical circuit (ASIC).

Furthermore, implementation of the invention including the further embodiments described is possible by means of a computer-readable storage medium on which is stored the computer program with program code.

The invention, including the further embodiments described below can also be implemented in a computer program product which has a storage medium on which is stored the computer program with program code which executes the invention.

The statistical distribution that forms the basis of the occurrence of the signals can be a statistical distribution of a first or a higher order. The higher order can be achieved by using an Edgeworth expansion, as described in Samuel Kotz, Norman L. Johnson (Editors-In-Chief), Cornish-Fisher and Edgeworth Expansions, Ch. 4, pages 188-192, Encyclopedia of Statistical Sciences, Volume 2, John Wiley & Sons, 1982 or a sum of normal distributions.

In such a statistical distribution of a higher order not only do mean value and covariance have to be matched to comply with a quantity of data—as in the case of such a statistical distribution of the first order—but further higher-order parameters like moments and cumulants also have to be matched.

It should be noted that the possibilities mentioned for achieving a higher order without restricting the generality are only two selected statistical distributions. Other possibilities are known to persons skilled in the art.

In addition, in the sum of normal distributions, the individual normal distributions and thus indirectly the neuronal activities can be weighted.

Optimization can also be implemented by means of a maximum likelihood estimation, as described in T. W. Anderson, An Introduction to Multivariable Statistical Analysis, Chapter 3, John Wiley & Sons, Inc., New York, London, Sydney, 1994 method.

In the optimization, a relationship between the linear statistical relationship and the statistical distribution can be taken into consideration as an auxiliary condition.

It is also expedient, because the biological model of neuronal structures can be mapped in a more real way, for external influences on the signals to be taken into consideration in the linear statistical relationship. Such external influences may, for example, be sensory inputs of sensory cells on the examined areas.

The determination of signals in the invention, for example of BOLD signals, can be carried out by measuring signals or by transferring and/or reading in existing signals.

The invention is particularly suitable for use in an fMRI technique, which is considerably improved and more powerful as a result.

In the context of such an fMRI use or fMRI examination, the neuronal areas are areas of the brain with corresponding nerve structures of patients to be examined and diagnosed.

In the fMRI examination using the inventive approach, BOLD signals are measured in various areas of the brain of a patient for defined perceptory or motor tasks carried out by the patient, which BOLD signals describe or represent the neuronal activities in the respective areas of the brain. These are evaluated or analyzed, whereby the signal coupling variables are determined.

Using the analysis results, in particular the signal coupling variables, functional as well as physical dependencies between areas of the brain can be detected and determined. These can further be used for a diagnosis concerning a functional disorder in an area of the brain of a patient, for example by comparing "disordered" dependencies with those of healthy persons.

DESCRIPTION OF THE PREFERRED EMBODIMENTS

The invention will be explained in the context of an embodiment for functional magnetic resonance imaging (fMRI).

Figure 1:
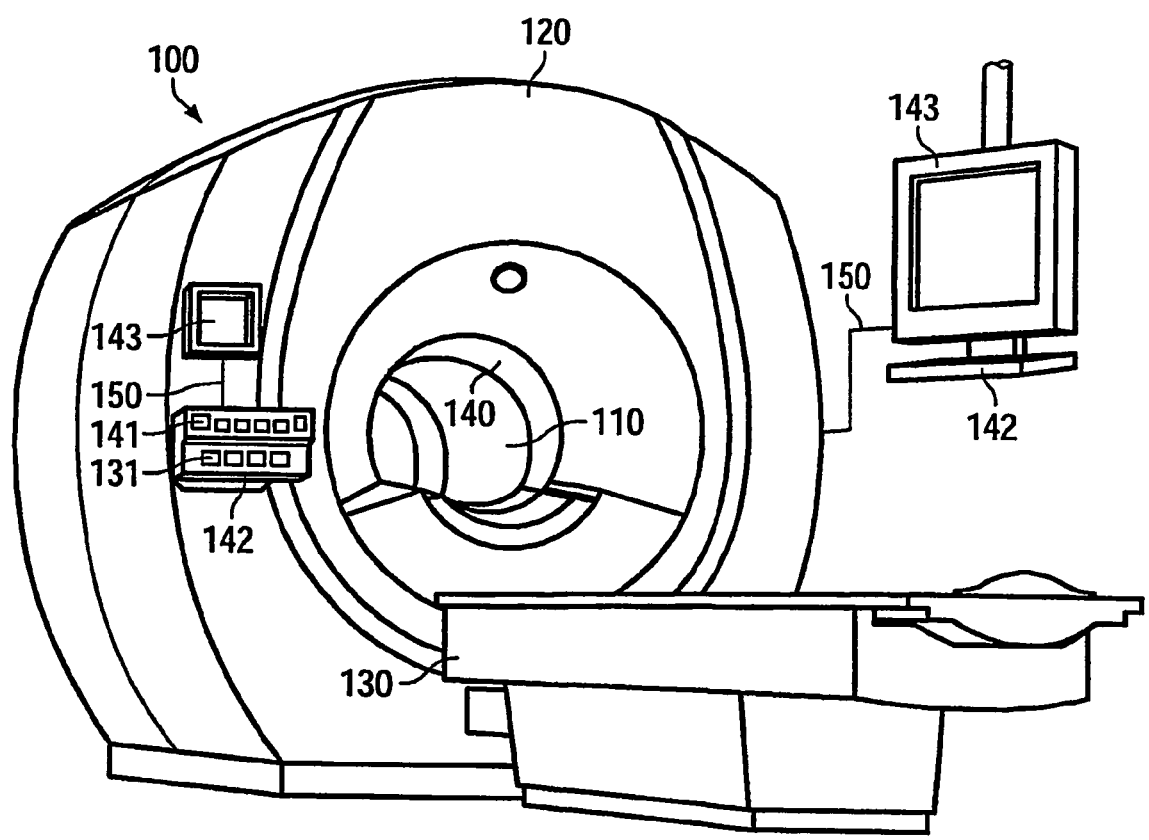
FIG. 1 illustrates a functional magnetic resonance imaging apparatus for conducting an fMRI examination in accordance with the invention.

FIG. 1 shows an apparatus 100 for carrying out functional magnetic resonance tomography (fMRI).

Basic principles of fMRI technology, which is a further development of the known modality of magnetic resonance tomography, are known from A. W. Toga and J. C. Maziotta (Ed.), "Brain Mapping: The Methods", Ch 9: M. S. Cohen: "Rapid MRI and Functional Applications", Academic Press 1996.

The apparatus 100 has a closed tunnel 110 which is incorporated in a magnet 120 such that it generates a strong magnetic field in the tunnel 110.

The apparatus 100 also has a patient table 130 that can be introduced into the tunnel 110, on which table a patient is placed for an examination.

In addition, the apparatus 100 has a control unit 131 that enables monitoring and control of the patient table 130 in the examination, for example a controlled introduction of the patient table 130 into the tunnel 120.

The tomography apparatus 100 also has a measuring device 140 for the measurement of BOLD (Blood Oxygenation Level Dependent) signals, an associated evaluation device 141 for evaluating the measured BOLD signals, in this case a high-performance computer, as well as an operating or interface device 142 for operating personnel and a display device 143 for displaying an examination result.

The components of the apparatus 100 are functionally connected to one another, for example via signal lines or data lines 150, via which the data and signals can be transferred.

Based on the fMRI technique, the neuronal activity in areas of the brain of a patient can be measured and analyzed and a diagnosis can be made by means of the apparatus 100 shown in FIG. 1.

To this end, the BOLD (Blood Oxygenation Level Dependent) signal in individual selected areas of the brain of the patient is measured by the measuring device 140, the BOLD signal being representation of the neuronal activity in the respective area.

The result of such fMRI measurements shows the curve of the activity of the individual areas over a certain period of time, for example during cognitive sequences as a result of specific perception processes or motor tasks which have to be carried out by the patient during an examination.

Functional disorders in the brain of the patient are thus inherently contained in the measured fMRI signals.

Using the evaluation device 141, which makes available or implements the inventive method of analysis, the fMRI measurements, i.e. the BOLD signals measured in individual areas of the brain, are analyzed.

This inventive method of analysis represents an improvement over the known method of analysis described above.

In the inventive method of analysis, brain activity is determined in the form of corresponding activation patterns in the examined areas in the brain and/or relationships between activation patterns in the examined areas and from that conclusions drawn directly of functional disorders in the brain and their causes.

The inventive of analysis made available by the evaluation device 140 is based upon an extended and more flexible model of the brain, of the neuron structures in the brain and their behavior, in particular their interactions, on the basis of which the measured BOLD signal is analyzed and evaluated.

The basic principles of the inventive method of analysis and the model are explained below.

The results or the conclusions of an examination are shown on the display device 143 and can be further processed by means of the operating and interface device 142 in connection with the evaluation device 141. They also serve as a basis for a medical diagnosis of a patient to be examined and diagnosed.

Figure 2:
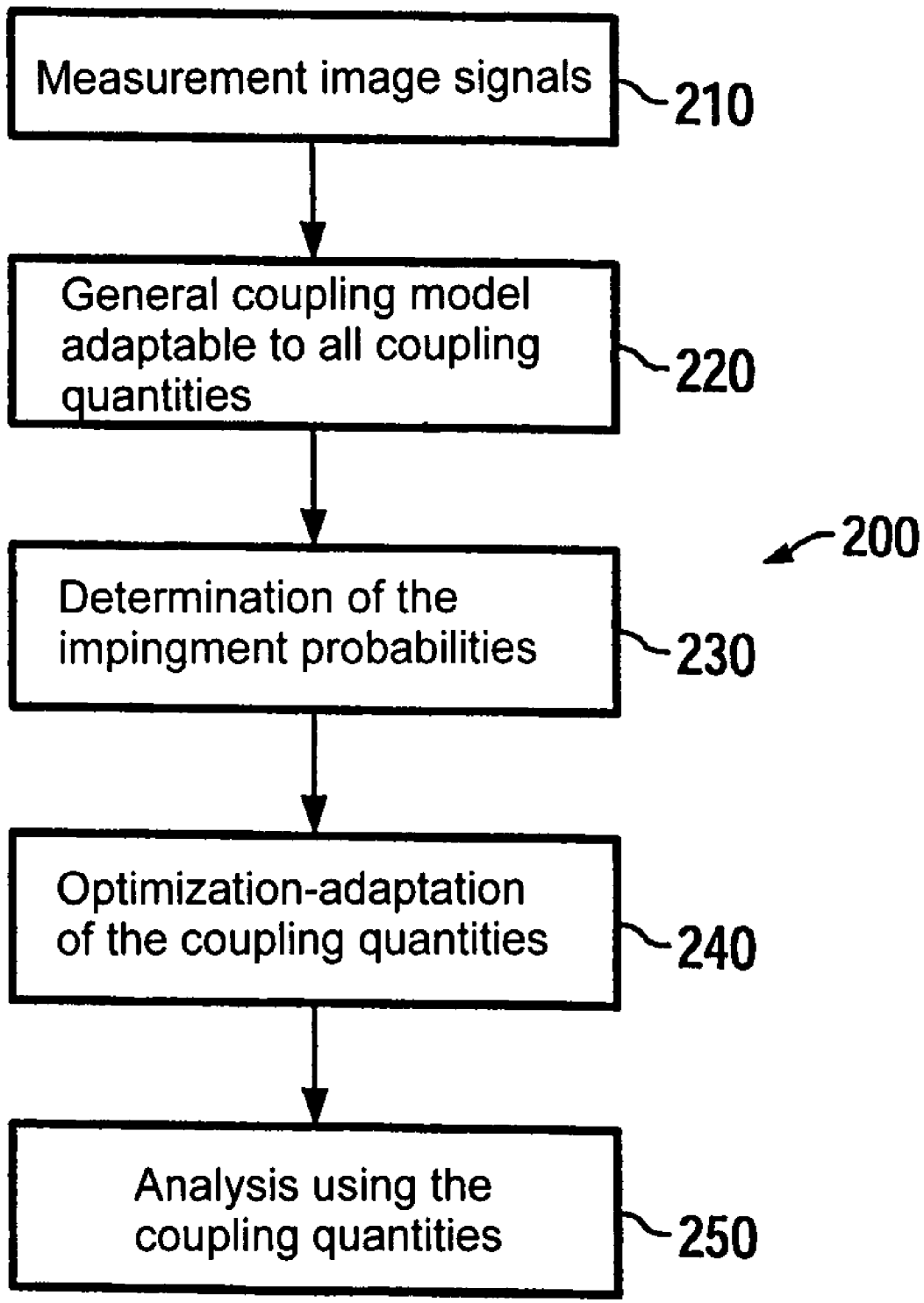
FIG. 2 is a flowchart for analyzing BOLD signals according to an exemplary embodiment of the invention.

Basic principles of the inventive method of analysis as set forth in FIG. 2, steps 210 to 250.

It should be noted that the inventive method of analysis is an improved further development of the known method of analysis described above. Consequently,—unless stated otherwise—the known and inventive method of analysis correspond in parts. Where matching parts are mentioned explicitly, they exhibit the labeling used previously hereinabove.

Using the inventive method of analysis 200 the fMRI measurements (210), i.e. the BOLD signals in examined areas of the brain of a patient, are analyzed (210 to 250) and/or compared with reference fMRI measurements. In this way, conclusions are drawn directly about functional disorders in the examined brain and their causes.

The inventive method of analysis 200, which generates statistical characteristic quantities, such as statistical correlations between fMRI measurements in various areas of the brain, is based on an extended and more flexible mathematical model (220) of the brain based upon the known mathematical model according to A. W. Toga and J. C. Maziotta (Ed.), "Brain Mapping: The Methods", Ch 9: M. S. Cohen: "Rapid MRI and Functional Applications", Academic Press 1996.

In this extended model (220) of the inventive method of analysis, the coupling matrix S is populated in all (matrix) positions by changeable coupling strengths $S_i$.

In the inventive method of analysis 200 all—because they are also changeable—coupling strengths Si are determined in such a way that statistical characteristic quantities which are determined from the fMRI measurements can best be explained (210 to 250).

A data point $s=s_t$ represents the totality of all the BOLD signals s1, . . . , sN of the individual n examined areas at a point in time t (or averaged over a time interval t) (t=[1;T]).

The fMRI measurement comprises a large number of such data points s1, s2, . . . , sT for differing perception processes and/or motor tasks for which the corresponding BOLD signals were measured.

In contrast to the known method of analysis, in which a multivariant standard distribution was assumed for the statistical distribution of the data points, in the new method of analysis 200 a weighted sum of normal distributions is assumed for the statistical distribution (220).

$$P(s \mid C_1, C_L, \mu_1, \ldots \mu_L, \Sigma_1, \ldots, \Sigma_L) = \frac{1}{\sum_{l=1}^{L} C_l} \cdot \sum_{l=1}^{L} \left\{ \frac{C_l}{\sqrt{2\pi}^N \cdot |\Sigma_l|} \cdot e^{-\frac{1}{2}(s-\mu_l)' \Sigma_l^{-1}(s-\mu_l)} \right\} \quad (5)$$

In this case, the chosen statistical distribution and thus also the equivalence of probabilities P=P(s|C1, . . . , CL, μ1, . . . , μL, Σ1, . . . , ΣL) (230) (cf. (2)) for the occurrence of measured data points s1, s2, . . . , sT depend on more or different parameters than the mean value μ and the covariance Σ of the known method of analysis.

In the inventive method of analysis 200 specific statistical variables, which can be calculated for the chosen statistical distribution, are now correlated with the model parameters, i.e. the coupling strengths $S_i$, the mean value με of external influence ε and the covariance Σε of ε.

These include inter alia the means values μ1, . . . , μL, the covariances Σ1, . . . , ΣL and all the moments and cumulants of the chosen distribution of a higher order.

An inherent relationship between the statistical distribution parameters and the model parameters to be determined emerges from this, in this case taking into consideration the distribution (5) and the extended model based upon the model according to (3).

$$\mu = \mu(C_1, C_L, \mu_1, \ldots, \mu_L, \Sigma_1, \ldots, \Sigma_L)$$

$$\Sigma = \Sigma(C_1, \ldots, C_L, \mu_1, \ldots, \mu_L, \Sigma_1, \ldots, \Sigma_L)$$

.

.

.

$$\mu = \mu(S, \mu_\epsilon, \mu)$$

$$\Sigma = \Sigma(S, \Sigma_\epsilon, \Sigma) \quad (6)$$

In conformance with the known method of analysis, the optimum model parameters are now determined (240) in an analogous manner in the new method of analysis 200 using maximum likelihood estimation [1] through optimization or maximization of the probabilities (5).

The basic principles of maximum likelihood estimation are described in T. W. Anderson, An Introduction to Multivariable Statistical Analysis, Chapter 3, John Wiley & Sons, Inc., New York, London, Sydney, 1994.

The parameters to be taken into consideration for the optimization are the parameters of the chosen statistical distribution of a higher order, in this case the weighted sum of normal distributions, the desired model parameters and statistical variables, in this case the mean value m and the covariance $\Sigma$ from (6), via which the relationships between the model parameters and the statistical distribution (5) were produced.

These relationships from (6) must be taken into consideration as auxiliary conditions in the optimization.

The optimization then leads to the desired coupling strengths $S_i$ that describe dependencies between the BOLD signals (250) and form the basis of the further evaluation and medical diagnosis (250).

As an alternative, in place of the weighted sum of normal distributions, the distribution of data points can be described by an Edgeworth expansion.

The basic principles of the Edgeworth expansion are described in Samuel Kotz, Norman L. Johnson (Editors-In-Chief), Cornish-Fisher and Edgeworth Expansions, Ch. 4, pages 188-192, Encyclopedia of Statistical Sciences, Volume 2, John Wiley & Sons, 1982.

Although modifications and changes may be suggested by those skilled in the art, it is the invention of the inventors to embody within the patent warranted heron all changes and modifications as reasonably and properly come within the scope of their contribution to the art.

The invention claimed is:

1. A method for analyzing neuronal activities in neuronal areas of a living subject, comprising the steps of:
    obtaining a plurality of signals from spatially distributed neuronal areas of a living subject, said signals respectively representing neuronal activity in different ones of said neuronal areas;
    automatically electronically forming a matchable coupling of all of said signals in said plurality of signals using matchable coupling variables that describe a statistical relationship between signals in said plurality of signals that are matchably coupled;
    automatically electronically determining respective probabilities for occurrence of said signals based on a higher order statistical distribution of the occurrence of said signals;
    automatically electronically determining said matchable coupling variables by optimizing said probabilities; and
    automatically electronically analyzing said neuronal activity using said matchable coupling variables to produce an analysis result and making said analysis result available in a humanly perceptible form.

2. A method as claimed in claim 1 comprising employing statistical distribution described by an Edgeworth expansion as said higher order statistical distribution.

3. A method as claimed in claim 1 comprising employing a sum of normal distributions as said higher order statistical distribution.

4. A method as claimed in claim 1 comprising optimizing said probabilities using a maximum likelihood estimation technique.

5. A method as claimed in claim 1 comprising employing a relationship between said statistical relationship and said statistical distribution in optimizing said probabilities.

6. A method as claimed in claim 1 wherein said signals in said plurality of signals are subject to external influences outside of said living subject, and employing said external influences to determine said statistical relationship.

7. A method as claimed in claim 1 comprising determining said plurality of signals by a measurement conducted with respect to said living subject.

8. A method as claimed in claim 7 comprising obtaining BOLD signals in said measurement as said plurality of signals.

9. A method as claimed in claim 1 comprising obtaining said plurality of signals from an area of the brain of said living subject, as said neuronal area.

10. A method as claimed in claim 1 comprising obtaining BOLD signals, as said plurality of signals, in a functional magnetic resonance imaging scan of said living subject.

11. A method as claimed in claim 1 comprising analyzing said matchable coupling variable associated with said BOLD signals to diagnose a functional disorder of said area of the brain of the living subject.

12. An arrangement for analyzing neuronal activities in neuronal areas of a living subject, comprising:
    a signal acquisition device adapted to interact with a living subject to obtain a plurality of signals from spatially distributed neuronal areas of the living subject, said signals respectively representing neuronal activity in different ones of said neuronal areas; and
    a computer supplied with said signals, said computer configured for electronically forming a matchable coupling of all of said signals in said plurality of signals using matchable coupling variables that describe a statistical relationship between signals in said plurality of signals that are matchably coupled, and electronically determining respective probabilities for occurrence of said signals based on a higher order statistical distribution of the occurrence of said signals, electronically determining said matchable coupling variables by optimizing said probabilities, and electronically analyzing said neuronal activity using said matchable coupling variables.

13. An arrangement as claimed in claim 12 wherein said signal acquisition device is an fMRI scanner and wherein said plurality of signals is a plurality of BOLD signals acquired by said fMRI scanner.

14. A computer-readable medium encoded with a data structure for analyzing neuronal activities in neuronal areas of a living subject from a plurality of signals obtained from spatially distributed neuronal areas of a living subject, said signals respectively representing neuronal activity in different ones of said neuronal areas, said data structure, when said medium is loaded into a computer, causing said computer to:
    form a matchable coupling of all of said signals in said plurality of signals using matchable coupling variables that describe a statistical relationship between signals in said plurality of signals that are matchably coupled;
    determine respective probabilities for occurrence of said signals based on a higher order distribution of the occurrence of said signals;
    determine said matchable coupling variables by optimizing said probabilities; and
    analyze said neuronal activity using said matchable coupling variables to produce an analysis result and making said analysis result available in a humanly perceptible form.

* * * * *